United States Patent [19]

Culley et al.

[11] Patent Number: 4,849,544

[45] Date of Patent: Jul. 18, 1989

[54] 1,3-DIAMINOCYCLOHEXANES

[75] Inventors: Scott A. Culley; Kestutis A. Keblys; Christopher J. Nalepa, all of Baton Rouge, La.

[73] Assignee: Ethyl Corporation, Richmond, Va.

[21] Appl. No.: 181,045

[22] Filed: Apr. 13, 1988

[51] Int. Cl.$^4$ ...................... C07C 85/24; C07C 87/36
[52] U.S. Cl. ..................................... 564/461; 564/451
[58] Field of Search ................... 564/451, 461; 528/64

Primary Examiner—Glennon H. Hollrah
Assistant Examiner—Peter G. O'Sullivan
Attorney, Agent, or Firm—Patricia J. Hogan

[57] ABSTRACT

Sterically hindered 1,3-diaminocyclohexanes which can be used in the preparation of polyurethane, polyurea, polyurethaneurea, and epoxy resins are prepared by hydrogenating a metaphenylenediamine having alkyl substituents of 1–6 carbons in the 4- and 6-positions and optionally also in the 2-position, at least one of the alkyl substituents containing at least two carbons, and the total number of carbons in the alkyl substituents being at least five, at a temperature of about 170°–200° C. and a pressure of at least about 6.9 MPa, preferably about 20–30 MPa, in the presence of a supported ruthenium catalyst and an activating amount of a modifier selected from alkali metal hydroxides and alkoxides and alkali metal amide salts of the meta-phenylenediamine to form the corresponding 1,3-diaminocyclohexane.

7 Claims, No Drawings

1,3-DIAMINOCYCLOHEXANES

FIELD OF INVENTION

This invention relates to 1,3-diaminocyclohexanes and more particularly to sterically hindered 1,3-diaminocyclohexanes which can be used in the preparation of polyurethane, polyurea, polyurethane-urea, and epoxy resins.

BACKGROUND

It is known that many diamines are useful as chain extenders or diisocyanate precursors in the preparation of polyurethane, polyurea, and polyurethane-urea polymers and as curing agents for epoxy resins. It is also known that cycloaliphatic diamines are apt to have the advantage of providing more color-stable products and that slower reacting diamines are sometimes desired to permit adequate time for processing.

It would be desirable to provide sterically hindered 1,3-diaminocyclohexanes which could be used in the aforementioned applications. However, most known processes for preparing cycloaliphatic amines from aromatic amines lead to such excessive hydrogenolysis in the hydrogenation of sterically hindered aromatic amines that the yield of diamine product is unacceptably low.

U.S. Pat. Nos. 3,697,449 (Brake) and 3,914,307 (Massie) show that some alkyl-substituted diaminocyclohexanes, viz., 1,4-diamino-2-methylcyclohexane, 1,3-diamino-2-methylcyclohexane, 1,2-diamino-3-methylcyclohexane, 1,3-diamino-2-methyl-4-ethyl-5,6-dipropylcyclohexane, are known; and Brake further teaches that cycloaliphatic amines can be prepared by the hydrogenation of aromatic amines in the presence of a supported ruthenium catalyst and an activating amount of an alkali metal hydroxide or alkoxide.

SUMMARY OF THE INVENTION

An object of this invention is to provide novel sterically hindered 1,3-diaminocyclohexanes.

Another object is to provide processes for preparing such 1,3-diaminocyclohexanes.

A further object is to provide polyurethane, polyurea, polyurethane-urea, and epoxy resins prepared from such 1,3-diaminocyclohexanes.

These and other objects are attained by (A) hydrogenating a meta-phenylenediamine having alkyl substituents of 1-6 carbons in the 4- and 6-positions and optionally also in the 2-position, at least one of the alkyl substituents containing at least two carbons, and the total number of carbons in the alkyl substituents being at least five, at a temperature of about 170°-200° C. and a pressure of at least about 6.9 MPa in the presence of a supported ruthenium catalyst and an activating amount of a modifier selected from alkali metal hydroxides and alkoxides and alkali metal amide salts of the meta-phenylenediamine to form the corresponding 1,3-diaminocyclohexane and (B) when desired, using the resultant 1,3-diaminocyclohexane to prepare a polyurethane, polyurea, polyurethane-urea, or epoxy resin.

DETAILED DESCRIPTION

Phenylenediamines which can be used in the practice of the invention are meta-phenylenediamines having alkyl substituents of 1-6 carbons, e.g., methyl, ethyl, propyl, isopropyl, butyl, sec-butyl, t-butyl, pentyl, hexyl, etc., substituents in the 4- and 6-positions and optionally also in the 2-position, at least one of the alkyl substituents containing at least two carbons, and the total number of carbons in the alkyl substituents being at least five. The preferred meta-phenylenediamines have at least two carbons in at least two of the alkyl substituents, and it is also frequently preferred that they have alkyl substituents in the 2-, 4-, and 6-positions. Exemplary of such compounds are 1,3-diamino-4,6-diisopropylbenzene, 1,3-diamino-2,4,6-triethylbenzene, 1,3-diamino-2,4-diethyl-6-methylbenzene, 1,3-di-amino-4,6-diethyl-2-methylbenzene, 1,3-diamino-4,6-dimethyl-2-isopropylbenzene, 1,3-diamino-2,4-dimethyl-6-isopropylbenzene, 1,3-diamino-4,6-diethyl-2-isopropylbenzene, 1,3-diamino-2,4-di-ethyl-6-isopropylbenzene, etc.

The supported catalysts, modifiers, and conditions used in the hydrogenation reaction are generally the same as those used in Brake (the teachings of which are incorporated herein in toto by reference) except that the modifier may be an alkali metal amide salt of the meta-phenylenediamine instead of an alkali metal hydroxide or alkoxide, the temperature should be in the range of about 170°-200° C., and the pressure must be at least about 6.9 MPa, preferably about 20-30 MPa. The activating amount of modifier employed is usually in the range of about 5-10%, based on the weight of catalyst; and a preferred modifier is potassium t-butoxide.

When it is desired to use an alkali metal amide salt as the modifier, it may be prepared by reacting the appropriate alkali metal hydride, e.g., sodium hydride, potassium hydride, etc., with the substituted meta-phenylenediamine. An alkali metal amide salt that is sometimes preferred is the sodium amide salt of a mixture of 1,3-diamino-2,4-diethyl-6-methylbenzene and 1,3-diamino-4,6-diethyl-2-methylbenzene.

The process of the invention leads to the formation of sterically hindered 1,3-diaminocyclohexanes in good yields with only minimal hydrogenolysis—a surprising result, since other known processes for preparing cycloaliphatic amines from aromatic amines lead to excessive hydrogenolysis when used for the hydrogenation of the sterically hindered meta-phenylenediamines employed in the present process. The 1,3-diaminocyclohexanes formed by the process are less colored than the meta-phenylenediamine starting materials and can be used in a variety of ways, e.g., as UV light stabilizers for polymers such as polypropylene; but they are of particular interest for use as chain extenders or diisocyanate precursors in the preparation of polyurethane, polyurea, and polyurethane-urea polymers and as curing agents for epoxy resins.

When the sterically hindered 1,3-diaminocyclohexanes are to be used as diisocyanate precursors, they are converted to the corresponding 1,3-cyclohexanediisocyanates by reaction with phosgene as in conventional processes for preparing isocyanates from amines. The 1,3-cyclohexanediisocyanates thus obtained, e.g., 4,6-diisopropyl-1,3-cyclohexanediisocyanate, 2,4,6-triethyl-1,3-cyclohexanediisocyanate, 2,4-diethyl-6-methyl,3-cyclohexanediisocyanate, 4,6-diethyl-2-methyl-1,3-cyclohexanediisocyanate, etc., can then be reacted with an active hydrogen-containing organic compound, such as a polyether diol, a polyester diol, or an amine-terminated polyether, and with a suitable chain extender, such as the known aliphatic, cycloaliphatic, and aromatic diamine and diol extenders or the substituted 1,3-diaminocyclohexanes of the present invention, to form polyurethane, polyurea, or polyurethane-urea polymers.

When the sterically hindered 1,3-diaminocyclohexanes are to be used as chain extenders in the preparation of polyurethane, polyurea, or polyurethane-urea polymers, they are simply substituted for the diamines that have previously been used in such processes or used in conjunction with known chain extenders. Thus, they are reacted with an organic polyisocyanate and an active hydrogen-containing organic compound or with a prepolymer thereof having a free -NCO content of at least 0.1% by weight to form the desired polymer. Exemplary of the isocyanates and active hydrogen-containing organic compounds that can be used are those taught in U.S. Pat. No. 4,595,742 (Nalepa et al.), the teachings of which are incorporated herein in toto by reference.

When the sterically hindered 1,3-diaminocyclohexanes are to be used as curing agents for epoxy resins, they are just substituted for the diamines that have previously been used to cure such resins or used in conjunction with known curing agents. The epoxy resin may be any epoxy resin, i.e., it may be saturated or unsaturated, aliphatic, cycloaliphatic, aromatic, or heterocyclic. Exemplary of such resins are those taught in Lee et al., *Handbook of Epoxy Resins*, McGraw-Hill (New York), 1967, the teachings of which are incorporated herein in toto by reference.

The following examples are given to illustrate the invention and are not intended as a limitation thereof.

EXAMPLE I

A suitable autoclave was charged with 11.1 g (0.058 mol) of commercial DETDA (a mixture of 1,3-diamino-2,4-diethyl-6methylbenzene and 1,3-diamino-4,6-diethyl-2-methylbenzene), 1.03g of 5% Ru on alumina, 0.16 g (1.4 mmol) of potassium t-butoxide, and 50 mL of t-butanol and pressurized to about 20.7 MPa hydrogen. The reaction mixture was then heated, and reaction samples were removed at various temperatures, viz.:

| Temp. (°C.) | Time (hrs.) | Conversion (%) | Yield (%) |
| --- | --- | --- | --- |
| 130 | 48 | 0 | |
| 150 | 5 | 0 | |
| 180 | 3 | 11 | |
| 190 | 20 | 93 | 90 |

The autoclave was then allowed to cool and its contents filtered. The solvent was removed from the filtrate in vacuo to give a clear liquid which was distilled through a 30.5 cm Vigreaux column at about 2 mm Hg and 80° C. to provide four colorless fractions. The third fraction (3.0 g) was determined by GC to be 97% pure. NMR, IR, MS, total amine titration, and elemental analyses were consistent with a mixture of 1,3-diamino-2,4-diethyl-6-methylcyclohexane and 1,3-diamino-4,6-diethyl-2-methylcyclohexane.

EXAMPLE II

Example I was essentially repeated except that the commercial DETDA was purified prior to the reaction, and 10 g (0.056 mol) of the purified DETDA was hydrogenated at 190° C. and about 24 MPa hydrogen for 21 hours to give 96% conversion and a 95% yield of the mixture of diaminodiethylmethylcyclohexanes.

EXAMPLE III

Example II was essentially repeated except that the reaction was carried out at 150° C. and about 10.3 MPa hydrogen for 18 hours, at which time GC indicated 31% conversion and an 87% yield. The temperature was then raised to 180° C., and the reaction was allowed to continue for 48 hours. Hydrogen absorption stopped after about 18 hours, and GC analysis of the reaction mixture showed 91% conversion and a 76% yield.

EXAMPLE IV

Following the same general procedure as in Example II, purified DETDA was hydrogenated at 190° C. and a hydrogen pressure of about 6.9 MPa in the presence of 1% Ru on alumina and 16% by weight of potassium t-butoxide, based on the weight of catalyst. After 17 hours GC analysis showed 12% conversion and a 73% yield.

EXAMPLE V

A suitable autoclave was charged with 1 g (0.052 mol) of purified 1,3-diamino-2,4,6-triethylbenzene, 0.15 g (1.2 mmol) of potassium t-butoxide, 1.0 g of 5% Ru on alumina, and 50 mL of t-butanol and heated to 190° C. at 25.5 MPa hydrogen for 17 hours. The autoclave was then cooled and its contents filtered. The solvent was removed from the filtrate in vacuo and the resulting liquid distilled through a 20.3 cm. Vigreaux column at about 1 mm Hg/187°–191° C. to give 6.8 g (66%) of 1,3-diamino-2,4,6-triethylcyclohexane.

EXAMPLE VI

A suitable autoclave was charged with 20.7 g (0.108 mol) of purified 1,3-diamino-4,6-diisopropylbenzene, 0.3 g (2.7 mmol) of potassium t-butoxide, 2.0 g of 5% Ru on alumina, and 100 mL of t-butanol. The autoclave was heated to 190° C. at 25.5 MPa hydrogen for 24 hours. It was then cooled and its contents filtered. The solvent was removed from the filtrate in vacuo and the resulting liquid distilled through a 20.3 cm Vigreaux column at about 4 mm Hg/115°–118° C. to give 5.9 g (28%) of 1,3-diamino-4,6-diisopropylcyclohexane.

EXAMPLE VII

A suitable reaction vessel was charged with 36g (0.2 mol) of commercial DETDA and 0.25g (0.011 mol) of sodium hydride. After the resultant solution had been stirred for about five minutes to convert part of the DETDA to the sodium amide salt, it was charged into an autoclave along with 3.4g of 5% Ru on alumina. The autoclave was heated to 190° C. at about 6.9 MPa hydrogen for 17 hours. GC analysis of the reaction mixture showed 31% conversion and a 55% yield.

EXAMPLE VIII

The reactivity of a mixture of 1,3-diamino-2,4-diethyl-6-methylcyclohexane and 1,3-diamino-4,6-diethyl-2-methylcyclohexane was evaluated by mixing 25 phr of the mixture with a commercial diglycidyl ether of bisphenol A having an epoxide equivalent of 190, placing a drop of the sample on a hot plate at the desired temperature, determining the gel time (i.e., the time elapsing until the epoxy resin no longer adhered to a spatula) at different temperatures, placing a drop of the sample in a Tg pan, scanning with a DSC at a heating rate of 10° C./minute from 30° C. to 300° C., determining the onset and peak exothermic temperatures, repeating the scan, and measuring the Tg. The gel times were determined to be 65 minutes at 115° C., 41 minutes at 130° C., 11 minutes at 170° C., and 3.2 minutes at 220° C. The onset temperature was 72° C., the peak temperature was 123° C., and the Tg was 59° C.

It is obvious that many variations can be made in the products and processes set forth above without departing from the spirit and scope of this invention.

What is claimed is:

1. A 1,3-diaminocyclohexane having alkyl substituents of 1-6 carbons in the 4- and 6-positions and optionally also in the 2-position, with the total number of carbons in the alkyl substituents being at least five.

2. The 1,3-diaminocyclohexane of claim 1 wherein at least two of the alkyl substituents contain at least two carbons.

3. The 1,3-diaminocyclohexane of claim 2 which is 1,3-diamino-4,6-diisopropylcyclohexane.

4. The 1,3-diaminocyclohexane of claim 2 which has alkyl substituents in the 2-, 4-, and 6-positions.

5. The 1,3-diaminocyclohexane of claim 4 which is 1,3-diamino-2,4,6-triethylcyclohexane.

6. The 1,3-diaminocyclohexane of claim 4 which is 1,3-diamino-2,4-diethyl-6-methylcyclohexane.

7. The 1,3-diaminocyclohexane of claim 4 which is 1,3-diamino-4,6-diethyl-2-methylcyclohexane.

* * * * *